United States Patent

Zenbayashi et al.

[11] Patent Number: 4,649,208
[45] Date of Patent: Mar. 10, 1987

[54] PROCESS FOR MAKING AMINO GROUP-CONTAINING ORGANOSILICON COMPOUNDS

[75] Inventors: Michio Zenbayashi; Noria Sato, both of Ohta, Japan

[73] Assignee: Toshiba Silicone Co., Ltd., Japan

[21] Appl. No.: 811,606

[22] Filed: Dec. 20, 1985

[30] Foreign Application Priority Data

Mar. 8, 1985 [JP] Japan ................... 60-46106

[51] Int. Cl.⁴ ............................ C07F 7/08; C07F 7/10; C07F 7/18
[52] U.S. Cl. ..................... 556/413; 556/425; 556/479
[58] Field of Search ............ 556/413, 425, 479

[56] References Cited

U.S. PATENT DOCUMENTS 3,795,656  3/1974  Martin ..................... 556/425 X
4,292,434  9/1981  Lindner et al. ............. 556/479

Primary Examiner—Paul F. Shaver

[57] ABSTRACT

A process for making an organosilicon compound containing an amino group, which comprises reacting an allylamine with the hydrosilyl group of a silicon compound represented by the formula:

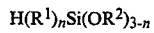

H(R$^1$)$_n$Si(OR$^2$)$_{3-n}$ wherein R$^1$ represents monovalent groups which may be identical of different and are selected from the group consisting of substituted or unsubstituted hydrocarbon groups, di- or trimethylsilyl groups and mono- or polyorganosiloxanyl groups; R$^2$ represents an alkoxy-substituted or unsubstituted alkyl group; and n represents an integer of 0 to 3, in the presence of a complex of platinum with an olefin or its derivative, said reaction being carried out further in the presence of an amino compound represented by the formula:

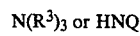

N(R$^3$)$_3$ or HNQ wherein R$^3$ represents monovalent groups which may be identical or different and are selected from the group consisting of hydrogen, alkyl groups and phenyl groups, at least one of which is an alkyl group or a phenyl group; Q represents a divalent group of the formula:

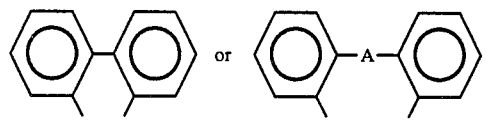

of which two valences are bonded to the same N atom; and A represents O or S.

6 Claims, No Drawings

PROCESS FOR MAKING AMINO GROUP-CONTAINING ORGANOSILICON COMPOUNDS

The present application claims priority of Japanese patent application serial no. 85/46106 filed Mar. 8, 1985.

BACKGROUND OF THE INVENTION

The present invention relates to a process for making an organosilicon compound containing an amino group, and more paticularly, to a process for making an organosilicon compound containing an amino group by reacting an allylamine with a silicon compound having hydrosilyl group, in the presence of a complex of platinum with an olefin or its derivative, and an amino compound within a defined scope, especially an aromatic amine compound. Also, the present invention provides a catalyst system which is high in reactivity for a wide variety of organosilicon compounds in the hydrosilylation reaction of allylamine.

For the preparation of an organosilicon compound containing an amino group, for example, an alkoxysilane containing a γ-aminoalkyl group, there have been heretofore employed methods requiring a large number of reaction steps and also an expensive reducing agent. To use the example of γ-aminopropyltriethoxysilane, acrylonitrile is allowed to react with trichlorosilane in the presence of an amine catalyst and a copper (I) chloride catalyst to obtain γ-cyanoethyltrichlorosilane, which is then converted to an alkoxy derivative by reaction with ethanol, followed by reduction with an expensive reducing agent such as $NaBH_4$ under high pressure to obtain γ-aminopropyltriethoxysilane. When trialkoxysilane is used as the starting material, the yield of γ-aminopropyltrialkoxysilane is markedly lowered.

As to the method in which allylamine is subjected to addition reaction with a silicon compound such as a silane or a siloxane having hydrosilyl group in the presence of a platinum catalyst, a large number of reports have been published. For example, N. S. Nametkin et al reported the reaction between triethoxysilane and allylamine in the presence of chloroplatinic acid, in which the yield of γ-aminopropyltriethoxysilane after the reaction at 100° C. for 6 hours was only 10% {Dokl. Akad. Nauk. SSSR. 140, 384 (1961)}, whereby allylaminotriethoxysilane is formed through side reactions to consume triethoxysilane. J. L. Speier reported the reaction with trialkoxysilane after protection of the amino group by trimethylsilylation, but such a method is not advantageous, because not only is the number of reaction steps increased, but also the yield of the silylation reaction is low to give a low total yield. West German Pat. No. 2,408,480 discloses a method in which an addition reaction is carried out to synthesize a cyclic silazane from a chlorosilane having hydrosilyl group and allylamine and the cyclilc silazane is cleaved with the use of an alcohol. However, this method is disadvantageous in that sufficient yield can only be obtained with difficulty, and cumbersome steps are required for removal of the salt.

Czechoslovakia Pat. Nos. 165,746, 193,448, 193,623, 194,149 and 200,379, U.K. Pat. No. 1,238,875 and East German Pat. No. 72,788 also disclose addition reactions between allylamine and alkoxysilane with platinum catalyst, but all of these methods employ chloroplatinic acid as the platinum catalyst and involve disadvantage such as requiring high temperature and long reaction time, for example, 125° C. and 56 hours, and poor reproducibility.

Otherwise, as the method for preparation of γ-aminopropyltrialkoxysilane, there is also the method in which γ-chloropropyltrialkoxysilane is aminated with ammonia or an amino compound, as disclosed in U.S. Pat. No. 4,234,503, but this is a high pressure reaction and also includes disadvantageously a large number of reaction steps.

SUMMARY OF THE INVENTION

The present inventors have conducted research to provide a method for obtaining an organosilicon compound containing an amino group with good yield by reaction under more mild conditions, and consequently found that a desired product can be obtained in high yield at a low temperature by using in combination a platinum complex having an olefin or its derivative as the ligand with an amino compound to accomplish the present invention.

DESCRIPTION OF THE INVENTION

More specifically, the present invention concerns a process for making an organosilicon compound containing an amino group, which comprises reacting an allylamine with the hydrosilyl group of a silicon compound represented by the formula:

$$H(R^1)_n Si(OR^2)_{3-n}$$

wherein $R^1$ represents monovalent groups which may be identical or different and are selected from the group consisting of substituted or unsubstituted hydrocarbon groups, di- or trimethylsilyl groups and mono- or polyorganosiloxanyl groups; $R^2$ represents an alkoxy-substituted or unsubstituted alkyl group; and n represents an integer of 0 to 3, in the presence of a complex of platinum with an olefin or its derivative, said reaction being carried out further in the presence of an amino compound represented by the formula:

$$N(R^3)_3 \text{ or } HNQ$$

wherein $R^3$ represents monovalent groups which may be identical or different and are selected from the group consisting of hydrogen, alkyl groups and phenyl groups, at least one of which is an alkyl group or a phenyl group; Q represents a divalent group of the formula:

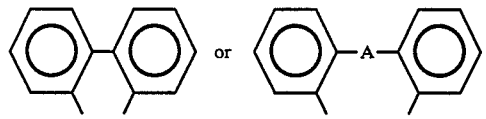

of which two valences are bonded to the same N atom; and A represents O or S.

The silicon compound having a hydrosilyl group to be used in the present invention may be a silane, a disilane, or a siloxane. In view of the prior art, when a silicon compound having an alkoxy group or a substituted alkoxy group bonded to a hydrosilyl group is prepared as a silane coupling agent, due to the presence of a carbon functional group and a silicon functional group, sufficient reactivity could not be obtained. Since this disadvantage has been overcome by the present invention, it is preferable to use a compound having an alkoxy group or a substituted alkoxy group bonded to the silicon atom of the hydrosilyl group, in other words, a compound wherein n is 0 to 2.

$R^1$ groups may be either identical or different and may include, for example, alkyl groups such as methyl, ethyl, propyl, butyl, pentyl, hexyl, octyl, decyl, etc.; alkenyl groups such as vinyl, allyl, etc.; aryl groups such as phenyl; aralkyl groups such as β-phenylethyl, β-phenylpropyl, etc.; substituted hydrocarbon groups such as cyanoethyl, 3,3,3-trifluoropropyl, chloromethyl, chloropropyl, etc.; and mono-, di-, tri- or tetrasiloxanyl groups in which the residual valences of the siloxanyl silicon atom are filled with hydrogen, methyl, phenyl, chlorine, methoxy, ethoxy, etc.; and siloxanyl groups with higher molecular weights. Methyl groups are preferred for easiness in synthesis, and siloxanyl groups are preferred when the objective product is a siloxane.

$R^2$ may be exemplified by alkyl groups such as methyl, ethyl, propyl, butyl, etc.; alkoxy-substituted alkyl groups such as methoxyethyl, ethoxyethyl, etc. For easiness in synthesis, reactivity and usefulness as a silane coupling agent, methyl groups or ethyl groups are preferred.

Non-limiting examples of such silicon compounds include alkoxysilanes and alkoxy-substituted alkoxysilanes such as trimethoxysilane, triethoxysilane, tripropoxysilane, tributoxysilane, tris(methoxyethoxy)silane, tris(ethoxyethoxy)silane, methyldimethoxysilane, methyldiethoxysilane, dimethylmethoxysilane, dimethylethoxysilane, phenyldimethoxysilane, phenyldiethoxysilane and the like; disilanes such as pentamethyldisilane, 1,1,2,2-tetramethyldisilane and the like; siloxanes such as pentamethyldisiloxane, 1,1,3,3-tetramethyldisiloxane, 1,1,1,3,5,5,5-heptamethyltrisiloxane and the like.

The platinum complex to be used in the present invention may be either zerovalent or divalent, or a mixture thereof, preferably zerovalent with respect to reactivity. As a specific feature of the present invention, by use of an olefin or its derivative as the ligand for the platinum complex, good reaction yield can be obtained under mild conditions. Examples of the ligand may include ethylene, octene, cyclooctadiene, mesityl oxide, vinylpentamethyldisiloxane, 1,3-divinyl-1,1,3,3-tetramethyldisiloxane, 1,3,5,7-tetravinyl-1,3,5,7-tetramethylcyclotetrasiloxane, polymethylvinylsiloxane, etc. A platinum catalyst containing no such olefin or its derivative as the ligand, for example, chloroplatinic acid is markedly low in yield or not reactive at all, and its reactivity is still poor even when used in combination with the amino compound of the present invention as hereinafter described.

The amount of olefin or its derivative complexed with platinum in the present invention is not particularly limited, but preferably is 10 ppm or more but less than 1,000 ppm as platinum atom based on the total weight of the reactants. At a level less than 10 ppm, the reaction proceeds too slowly to give a good yield within a short time. By use of an amount of 1,000 ppm or higher, no particular additional effect can be obtained.

The amount of allylamine is not particularly limited, but preferably is about equimolar relative to the hydrosilyl group of the silicon compound.

Another specific feature of the present invention resides in an amino compound other than allylamine. Even if the complex of platinum with an olefin or an olefin derivative as described above may be employed, when no amino compound is used in combination therewith, the reaction will not proceed or gives low yield if the reaction does proceed. Of the amino compounds, the HNQ type compounds are more preferred than the $N(R^3)_3$ type compounds with respect to reactivity. As such amino compounds, those of the $N(R^3)_3$ type may include, for example, triethylamine, tributylamine, dibutylamine, dihexylamine, n-hexylamine, n-octylamine, N-methylaniline and the like. Amino compounds of the HNQ type may include carbazole, phenoxazine and phenothiazine.

The amount of the amino compound added is not particularly limited, but it is preferably within the range of from 0.001 to 10% by weight based on the total weight of the reactants. At a level less than 0.001% by weight, the reactivity becomes poor, whereas the platinum complex may be inactivated at a level in excess of 10% by weight.

The reaction conditions are not particularly limited, but the reaction can proceed under normal pressure and relatively mild heating conditions such as 40° to 110° C. to give a silicon compound containing an amino group in good yield.

According to the present invention, it has become possible to carry out the reaction of allylamine with a silicon compound having a hydrosilyl group, particularly alkoxysilanes under mild conditions in good yield. Also, according to the present invention, an advantageous process for making an organosilicon compound having a γ-aminopropyl group, particularly γ-aminopropyltrialkoxysilane, was obtained.

EXAMPLES OF THE INVENTION

The present invention is further described by referring to the following Examples, in which parts are parts by weight.

Example 1

Into a reactor equipped with a reflux condenser, a thermometer, a dropping funnel and a stirrer, 11.4 parts of allylamine, 0.4 part of phenothiazine and 0.0002 part as platinum atom of zerovalent platinum-mesityloxide complex were charged, and the mixture heated with stirring to 60° C. While maintaining the mixture at that temperature, 32.8 parts of triethoxysilane were gradually added dropwise through the dropping funnel. The dropwise addition was completed in 25 minutes, and the liquid temperature was elevated up to 110° C. over 3 hours in an oil bath, while continuing stirring. A sample was taken from the reactor and subjected to analysis by gas chromatography to find that allylamine and triethoxysilane were almost completely consumed.

The reaction product was cooled and distilled with addition of 1.0 part of ethanol to obtain 33.2 parts of γ-aminopropyltriethoxysilane boiling at 124° to 125° C./35 Torr. This corresponded to 75% yield based on the theoretical amount.

Example 2

Into the same reactor as used in Example 1, 54.7 parts of allylamine, 1.0 part of phenothiazine and 0.0005 part as platinum atom of the same platinum complex as in Example 1 were charged, 100 parts of dimethylethoxysilane were added at 50° C. through the dropping funnel over 20 minutes, and the reaction was completed by elevating the temperature to 125° C. over 4 hours.

After cooling, 5.5 parts of ethanol were added, and distillation was carried out to give 87.8 parts of γ-aminopropyldimethylethoxysilane boiling at 75° to 77° C./18 Torr. This corresponded to 55% yield based on the theoretical amount.

Example 3

Into the same reactor as used in Example 1, 17.1 parts of allylamine, 0.3 part of carbazole, 0.00005 part as platinum atom of the same platinum complex as in Example 1 were charged, 31.8 parts of methyldimethoxysilane were added dropwise at 40° C. over 5 minutes, followed further by continuing stirring for 4 hours while maintaining the liquid temperature at 60° C. After cooling, 1.7 parts of ethanol were added and distillation was carried out to give 36.2 parts of γ-aminopropylmethyldimethoxysilane boiling at 105° to 109° C./50 Torr. This corresponded to 74% yield based on the theoretical amount.

The same reaction was carried out by use of 0.3 part of phenothiazine in place of carbazole. As a result, the yield of γ-aminopropylmethyldimethoxysilane was 35.2 parts, which corresponded to 72% yield based on the theoretical amount.

Example 4

Methyldimethoxysilane was replaced with 44.4 parts of pentamethyldisiloxane and the reaction conditions were changed to 60° C. and 8 hours, and, following otherwise the same conditions as in Example 1, 33.8 parts of γ-aminopropylpentamethyldisiloxane were obtained. This corresponded to 55% yield based on the theoretical amount.

Example 5

Synthetic experiments 51 to 55 for preparation of γ-aminopropyltriethoxysilane were conducted in the same manner as in Example 1 except for changing the platinum complex and its amount as shown in Table 1. The yields, yield percentages based on the theoretical amounts of the objective products are as shown in Table 1.

TABLE 1

| Experiment No. | Platinum complex Kind | Amount parts* | Yield parts | Yield percentage % |
|---|---|---|---|---|
| 51 | Platinum-ethylene complex | 0.0002 | 16.4 | 37 |
| 52 | Platinum-octene complex | 0.0003 | 14.6 | 33 |
| 53 | Platinum-vinyl pentamethyl disiloxane complex | 0.0002 | 31.8 | 72 |
| 54 | Platinum-poly(methylvinyl-siloxane)complex | 0.0002 | 31.0 | 70 |
| 55 | Platinum-cyclo-octadiene complex | 0.0002 | 23.4 | 53 |

*the amount as calculated on platinum atom

Example 6

In the same manner as in Example 1 except for changing the amino compound and its amount as shown in Table 2, synthetic experiments 61 to 65 for preparation of γ-aminopropyltriethoxysilane were conducted. The yields, the yield percentages based on the theoretical amounts of the objective products are as shown in Table 2.

TABLE 2

| Experiment No. | Amino compound Kind | Amount, parts | Yield parts | Yield percentage % |
|---|---|---|---|---|
| 61 | Phenoxazine | 0.5 | 39.3 | 89 |
| 62 | Carbazole | " | 40.1 | 91 |
| 63 | Diphenylamine | " | 28.7 | 65 |
| 64 | Triethylamine | " | 25.6 | 58 |
| 65 | Hexylamine | " | 27.4 | 62 |

Comparative example

In the same manner as in Example 1 except for changing the kinds of platinum compound and amino compound and their amounts to those as shown in Table 3, synthetic experiments 71 to 73 for preparation of γ-aminopropyltriethoxysilane were conducted. In experiments 71 and 72, platinum compounds outside the scope of the present invention were employed, while in experiments 72 and 73, no amino compound was employed. In none of these experiments, formation of γ-aminopropyltriethoxysilane could be recognized.

TABLE 3

| Experiment No. | Platinum compound Kind | Amount parts* | Amino compound Kind | Amount parts |
|---|---|---|---|---|
| 71 | Chloroplatinic acid hexahydrate | 0.0005 | Phenothiazine | 0.5 |
| 72 | Chloroplatinic acid hexahydrate | 0.01 | — | — |
| 73 | Platinum-vinyl pentamethyl di-siloxane complex | 0.0003 | — | — |

*the amount as calculated on platinum atom

We claim:

1. A process for making an organosilicon compound containing an amino group, which comprises reacting an allylamine with the hydrosilyl group of a silicon compound represented by the formula:

$$H(R^1)_n Si(OR^2)_{3-n}$$

wherein $R^1$ represents monovalent groups which may be identical or different and are selected from the group consisting of substituted or unsubstituted hydrocarbon groups, di- or trimethylsilyl groups and mono- or polyorganosiloxanyl groups; $R^2$ represents an alkoxy-substituted or unsubstituted alkyl group; and n represents an integer of 0 to 3, in the presence of a complex of platinum with an olefin or its derivative, said reaction being carried out further in the presence of an amino compound represented by the formula:

$$N(R^3)_3 \text{ or } HNQ$$

wherein $R^3$ represents monovalent groups which may be identical or different and are selected from the group consisting of hydrogen, alkyl groups and phenyl groups, at least one of which is an alkyl group or a phenyl group; Q represents a divalent group of the formula:

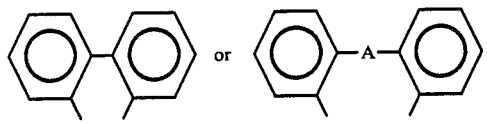

of which two valences are bonded to the same N atom; and A represents O or S.

2. A process for making an organosilicon compound containing an amino group according to claim 1, wherein n is 0 to 2.

3. A process for making an organosilicon compound containing an amino group according to claim 1, wherein $R^1$ is a methyl group.

4. A process for making an organosilicon compound containing an amino group according to claim 1, wherein $R^2$ is an alkyl group having 1 or 2 carbon atoms.

5. A process for making an organosilicon compound containing an amino group according to claim 1, wherein the amino compound is HNQ.

6. A process for making an organosilicon compound containing an amino group, which comprises reacting an allylamine with the hydrosilyl group of a silicon compound selected from the group consisting of a silane, a disilane, or a siloxane, in the presence of a complex of platinum with an olefin or its derivative, said reaction being carried out further in the presence of an amino compound represented by the formula $N(R^3)_3$ or HNQ wherein $R^3$ represents monovalent groups which may be identical or different and are selected from the group consisting of hydrogen, alkyl groups and phenyl groups, at least one of which is an alkyl group or a phenyl group; Q represents a divalent group of the formula:

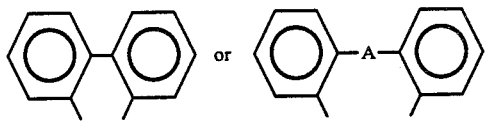

of which two valences are bonded to the same N atom; and a represents O or S.

* * * * *